United States Patent [19]

Nobuaki et al.

[11] Patent Number: 4,609,814

[45] Date of Patent: Sep. 2, 1986

[54] CONTROL FOR OPERATION MICROSCOPES

[75] Inventors: Kitajima Nobuaki; Nishimura Shinichi; Takahashi Susumu, all of Tokyo, Japan

[73] Assignee: Tokyo Kogaku Kikai Kabushiki Kaisha, Japan

[21] Appl. No.: 621,505

[22] Filed: Jun. 18, 1984

[30] Foreign Application Priority Data

Jun. 20, 1983 [JP] Japan .................. 58-110726
Jun. 20, 1983 [JP] Japan .................. 58-110727

[51] Int. Cl.⁴ .................. G01J 1/20; G01B 11/00
[52] U.S. Cl. .................. 250/201; 356/400
[58] Field of Search ........... 250/201 AF, 201 R, 204; 356/400

[56] References Cited

U.S. PATENT DOCUMENTS

3,721,827  3/1973  Reinheimer .................. 250/201

Primary Examiner—Gene Wan
Attorney, Agent, or Firm—Brumbaugh, Graves, Donohue & Raymond

[57] ABSTRACT

An operation microscope system comprising an operation microscope including an observation optical system adapted for observing a portion of a patient wherein an operation is to be made. A mark device is provided on one of the microscope and the patient's portion and a mark position detector is provided on the other.

A control circuit is provided and has a memory for memorizing an initial position signal as produced by the detector when an initial focus condition or a visual field is established between the patient's portion and the microscope and an out-of-focus condition or a change in the visual field is detected by a relative displacement between the patient's portion and the microscope based on the initial position signal and an actual position signal as produced by the detector to produce a correcting signal to thereby restore the initial focus condition or the initial visual field.

10 Claims, 13 Drawing Figures

CONTROL FOR OPERATION MICROSCOPES

BACKGROUND OF THE INVENTION

1. Field of the Invention

The present invention relates to operation microscopes and more particularly to a control of operation microscopes. More specifically, the present invention pertains to an automatic control of a relative position between an operation microscope and a patient.

2. Description of Prior Art

In some fields of medical professions such as ophthalmology and otorhinolaryngology, operation microscopes have long been used in operations since organs which are to be subjected to operations are of fine tissues. In operations using such microscopes, patients are anesthetized normally only in those portions where the operations are made so that it is very likely that the patients move during the operations. Further, there are possibilities that structures supporting the microscopes be slightly moved due to various reasons. Therefore, the microscopes are very often moved during operations with respect to the patients necessitating readjustment of visual fields and focus conditions.

In conventional operation microscopes, there have therefore been provided fine adjusting mechanisms for moving the optical systems of the microscopes in planes perpendicular to the optical axes thereof to adjust the visual fields and for moving the focusing optical elements along the optical axes to adjust the focus conditions. These fine adjusting mechanisms are operated electrically through actuations of foot pedal switches. It should however be noted that due to developments in the instruments which are used directly or indirectly for performing operations, there are provided foot pedal switches which usually amount to 10 to 20 so that operators may have difficulties even in keeping the locations of the switches in memory. Therefore, there is a danger that the foot pedal switches are erroneously operated.

OBJECT OF THE INVENTION

It is therefore an object of the present invention to provide an operation microscope system which can automatically restore a previously determined relative position between the microscope and the patient even when there is produced a change in the relative position.

Another object of the present invention is to provide an operation microscope in which an initially established focus condition can be automatically maintained throughout the operation.

A further object of the present invention is to provide a combination of an operation microscope and an operation bed in which a previously determined relative position can be automatically maintained between the microscope and the patient.

Still further object of the present invention is to provide an operation microscope system including an operation microscope and a patient support in which relative position of the microscope and the patient support can be automatically adjusted to maintain an initially established visual field of the microscope.

SUMMARY OF THE INVENTION

According to the present invention, the above and other objects can be accomplished by an operation microscope system comprising operation microscope means including observation optical means having an observing optical axis and adapted for observing at least a portion of a patient wherein an operation is to be made, support means for supporting said microscope means and at least said portion of the patient for relative movement, driving means for effecting a relative movement between said portion of the patient and said microscope means, mark means provided on one of said microscope means and said patient, mark detecting means provided on the other of the microscope means and said patient for receiving beams from said mark means to produce a position signal in accordance with a relative position between the mark means and the mark detecting means, memory means for memorizing an initial position signal as produced by said detecting means when an initial relative position is established between said portion of the patient and said microscope means, displacement detecting means for detecting a relative displacement between said portion of the patient and the microscope means based on said initial position signal and an actual position signal as produced by said mark detecting means to produce a displacement signal, adjusting means for actuating said driving means in accordance with said displacement signal to restore said initial relative position.

According to a preferable aspect of the present invention, said support means includes means for supporting said microscope means and said portion of the patient so that a relative movement is allowed between said portion of the patient and the microscope means at least in a plane perpendicular to the observing optical axis for a visual field adjustment, said driving means including means for effecting the relative movement in said plane. In one mode of the present invention, said support means includes a patient support for supporting at least said portion of the patient for movement with respect to the microscope means. In another mode, the support means may include means for supporting the microscope means for movement with respect to said portion of the patient.

In another aspect of the present invention, the support means includes means for supporting said microscope means and said portion of the patient so that a relative movement is allowed between said portion of the patient and the microscope means in a direction parallel to said optical axis for focusing, said driving means including means for effecting the relative movement along said optical axis. The support means may include a patient support for supporting at least said portion of the patient for movement in the direction parallel to the optical axis. Alternatively, the microscope means may be provided with focusing means and the driving means may include means for driving the focusing means.

BRIEF DESCRIPTION OF THE DRAWINGS

In the accompanying drawings.

DESCRIPTION OF THE PREFERRED EMBODIMENTS

Present invention will now be described with reference embodiments applied to operation microscopes for ophthalmology, however, it should be noted that the invention can well be applied to operation microscopes adapted to be used in other fields such as otorhinolaryngology.

Figure 1:
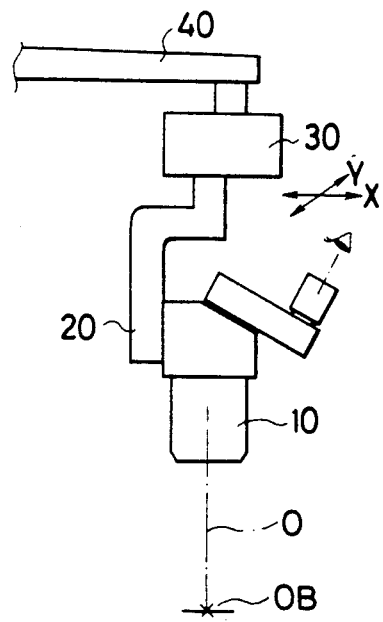
FIG. 1 is a side view of an operation microscope which may be used in the system embodying the features of the present invention.

Referring to the drawings, particularly to FIG. 1, there is shown an operation microscope including an observing optical system 10 having an optical axis O and carried by a support arm 20 which is in turn carried by a fine adjustment device 30 so that the support arm 20 and the operation microscope carried thereon can be moved in a plane perpendicular to the optical axis O along to perpendicularly crossing axes X and Y. The fine adjustment device 30 is attached to an articulated arm mechanism 40 which is swingably mounted on a stationary support (not shown). The operation microscope is placed above a patient's portion OB such as an eye wherein an operation is to be made so that the portion OB can be observed with a high magnification power.

Figure 2:
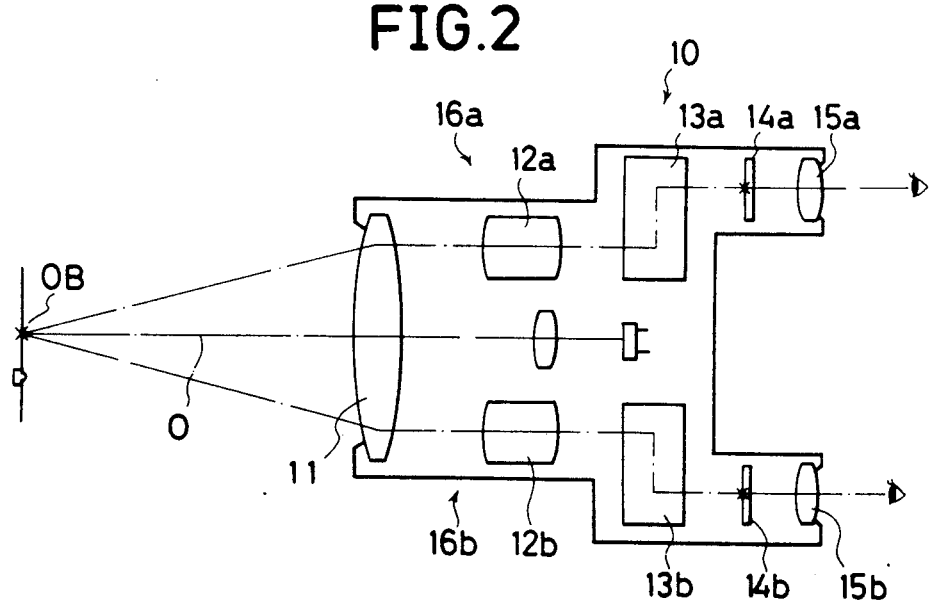
FIG. 2 is a diagrammatical illustration of the optical system in the microscope.

The observing optical system 10 includes, as shown in FIG. 2, an objective lens 11 having the aforementioned optical axis O and adapted to be placed opposite to the portion OB to be operated. Behind the objective lens 11, there are a pair of power changing lenses 12a and 12b which are disposed at the opposite sides of and in parallel with the optical axis O. Further behind the power changing lenses 12a and 12b, there are arranged image inverting prisms 13a and 13b, imaging plates 14a and 14b and eye pieces 15a and 15b to constitute a binocular observing system having a pair of symmetrical optical systems 16a and 16b.

Figure 3:
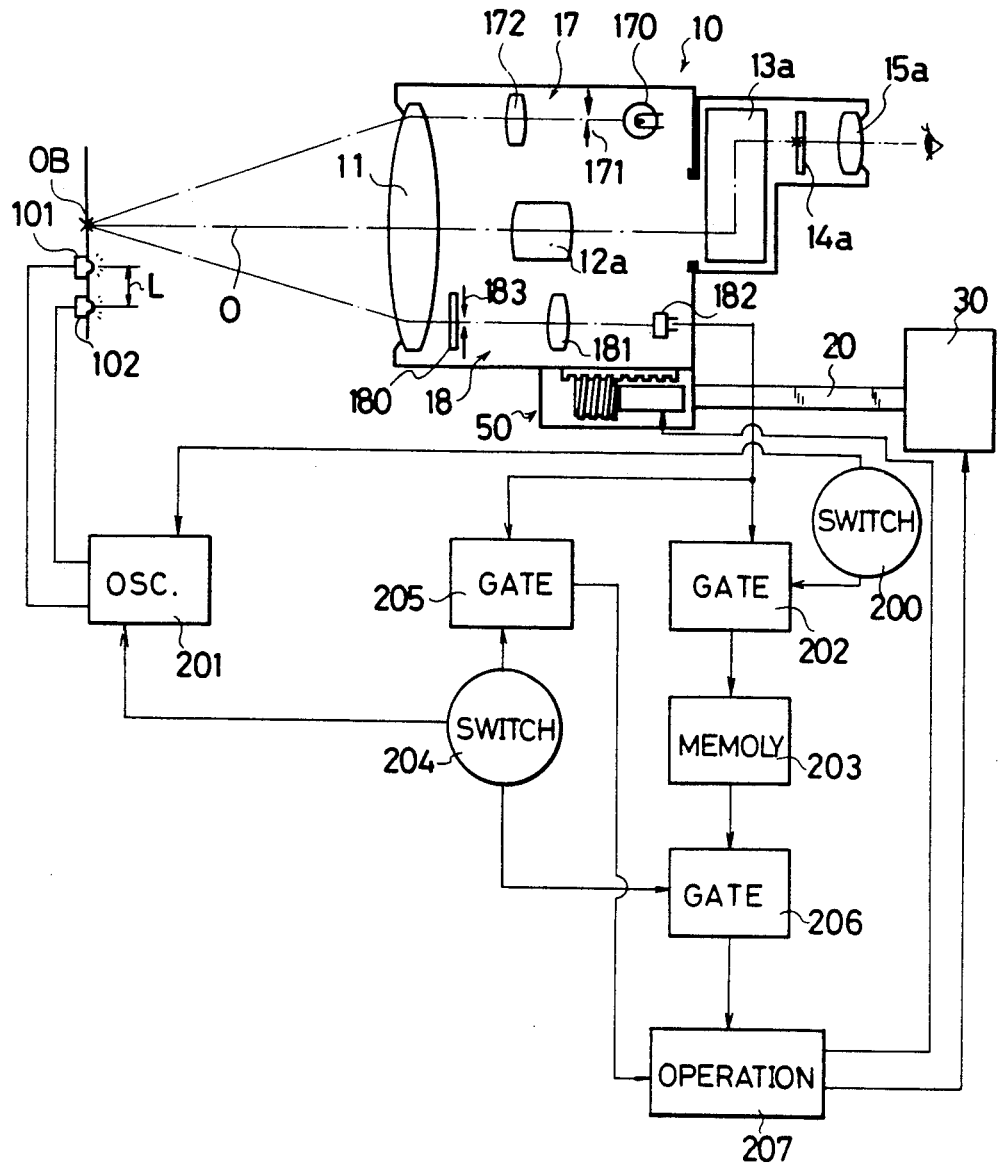
FIG. 3 is a diagrammatical illustration of the operation microscope system in accordance with one embodiment of the present invention.

Referring to FIG. 3, it will be noted that the observing optical system 10 includes an illumination optical system 17 and a detecting optical system 18 which are arranged in a plane perpendicular to a plane in which the optical systems 16a and 16b are arranged. The illumination optical system 17 includes a light source 170, an aperture 171 and a projecting lens 172 so that beams of light are passed from the light source 170 through the objective lens 11 to the object OB. The detecting optical system 18 includes a filter 180 which is disposed behind the objective lens 11. Behind the filter 180, there is an imaging lens 181. An aperture 183 is disposed at the front focal point of the lens 181 and detector 182 comprised of a two-dimensional arrays of photoelectrical elements and located at the back focal point of the lens 181. The observing optical system 10 is connected with a focusing mechanism 50 which is housed in the support arm 20 so that the observing optical system 10 is moved along the optical axis O to and away from the object OB to focus the optical system 10 on the object OB.

Figure 4:
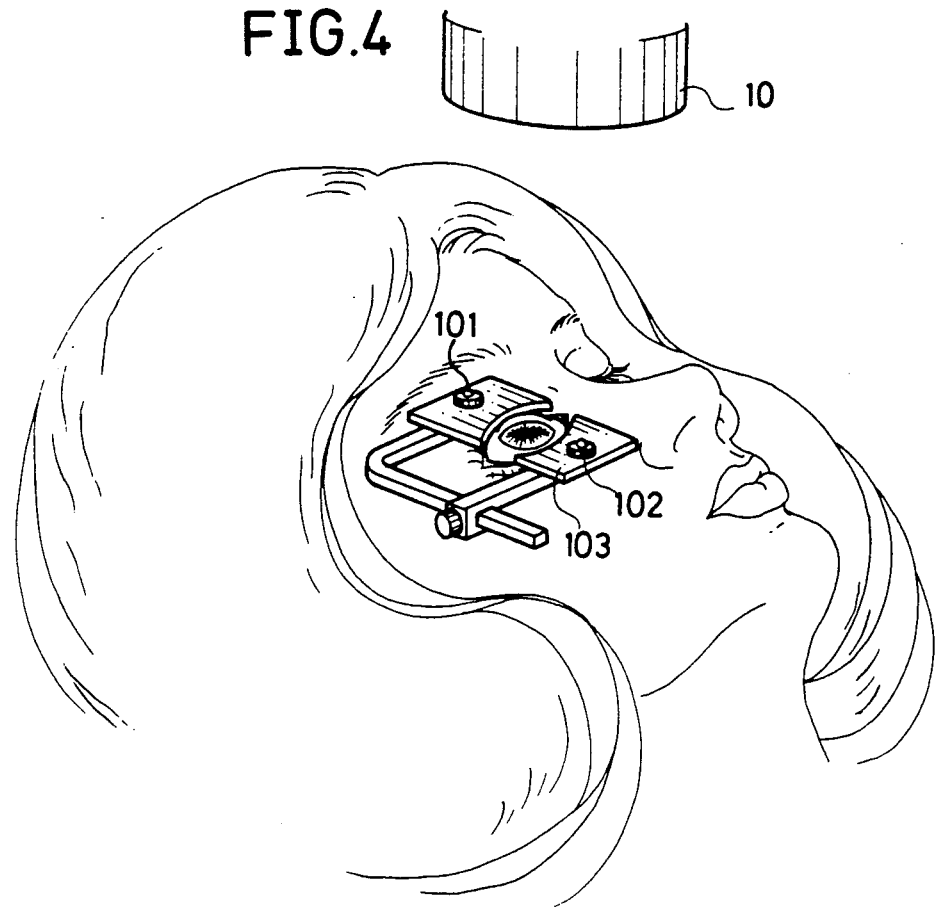
FIG. 4 is a perspective view showing an example of the mark projecting device.

For the purpose of aligning and focusing the optical system 10 with respect to the portion OB to be operated such as a patient's eye, there are provided a pair of light-emitting-diodes 101 and 102 as shown in FIG. 4. Two diodes are required for the purpose of focusing so that only one diode may be used in case where only the alignment is necessary. In the example shown in FIG. 3, the diodes 101 and 102 are mounted on an eye-opener 103 which is usually used in an eye operation.

In FIG. 3, there is shown an automatic alignment and focusing control system which includes an oscillator 201 which produces signals for alternately energizing the diodes 101 and 102. The light beams from the diodes 101 and 102 are passed through the objective lens 11, the filter 180 and the aperture 183 to the focusing lens 181 to be focused thereby on the detector 182. In order to control the operation of the oscillator 201, there is provided an initial value setting switch 200.

The output of the detector 182 is connected with a gate circuit 202 which is adapted to be opened by the actuation of the switch 200 so that the output of the detector 182 is passed to a memory circuit 203. The memory circuit 203 memorizes the informations concerning the locations of the images of the diodes 101 and 102 produced on the detector 182 as values on X-Y coordinates. A readout gate circuit 206 is provided for reading out the memories in the memory circuit 203. The signals which have passed through the gate circuit 206 is applied to an operation circuit 207.

The output of the detector 182 is also connected with a gate circuit 205 which is opened by a modifying switch 204. The gate circuit 205 allows the signals from the detector 182 to pass to the operation circuit 207 when it is opened by the switch 204. The modifying switch 204 further functions to operate the oscillator 201 and to open the read out gate 206.

In operation, an operator at first determines the position of the observing optical system 10 of the operation microscope so that the optical system 10 is aligned with the object OB and appropriately focused thereon. Then, the switch 200 is turned on to energize the oscillator 201 so that the diodes 101 and 102 are alternately energized.

The light beams from the diodes 101 and 102 are then focused on the detector 182 which produces signals carrying informations concerning the locations of the images of the diodes 101 and 102 on the detector 182. The actuation of the switch 200 opens the gate circuit 202 so that the signals from the detector 182 are passed to the memory circuit 203. After the signals from the detector 182 are thus memorized, the switch 200 is manually or automatically turned off.

When it is found during operation that the visual field and/or the focus condition of the microscope have been changed, the operator actuates the modifying switch 204 to open the gates 205 and 206 and energize the oscillator 201. The diodes 101 and 102 are then energized alternately to emit beams of light which are focused on the detector 182. The signals from the detector 182 are passed through the gate 205 to the operation circuit 207. The informations concerning the initial values are read out through the gate circuit 206 and passed to the operation circuit 207.

The operation circuit 207 then carries out an operation based on the actual position signals from the detector 182 and the initial position signals from the memory circuit 203. The operation is carried out by the following formula.

$$\delta_x = (x_1 - x_0)\beta^{-1}$$

$$\delta_y = (y_1 - y_0)\beta^{-1}$$

$$\delta_l = \sqrt{(x_0 - x_0')^2 + (y_0 - y_0')^2} - \sqrt{(x_1 - x_1')^2 + (y_1 - y_1')^2}$$

$$\delta_z = \frac{f}{\beta^2} \frac{\delta l}{L}$$

where:
- $x_o$ and $y_o$ are coordinate values of the initial position of the image of the diode 101 on the detector 182;
- $x_o'$ and $y_o'$ are coordinate values of the initial position of the image of the diode 102 on the detector 182;
- $x_1$ and $y_1$ are coordinate values of the actual position of the image of the diode 101 on the detector 182;
- $x_1'$ and $y_1'$ are coordinate values of the actual position of the image of the diode 102 on the detector 182;
- $\beta = f_2/f_1$;
- $f_1$ is the focal distance of the objective lens 11;
- L is the distance between the diodes 101 and 102;
- $f_2$ is the focal distance of the lens 181;
- $f_1$ is the composite focal distance of the lenses 11 and 181;
- $\delta_x$ and $\delta_y$ are displacements in x and y directions, respectively, between the initial position and the actual position;
- $\delta_z$ is the displacement along the optical axis O.

Figure 5:
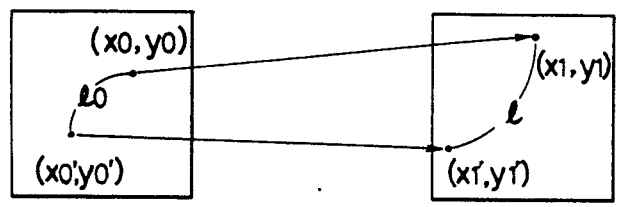
FIG. 5 is a diagram illustrating an example of displacements of projected marks on the detecting means.

In FIG. 5, there are shown the initial and actual positions of the images of the diodes. The operation circuit 207 thus produces outputs concerning the displacements $\delta_x$ and $\delta_y$ and applies these outputs to the fine adjustment device 30 to thereby correct the visual field. Further, the operation circuit 207 produces an output concerning the displacement $\delta_z$ and applies it to the focusing mechanism 50 to correct the focus condition.

Figure 10:
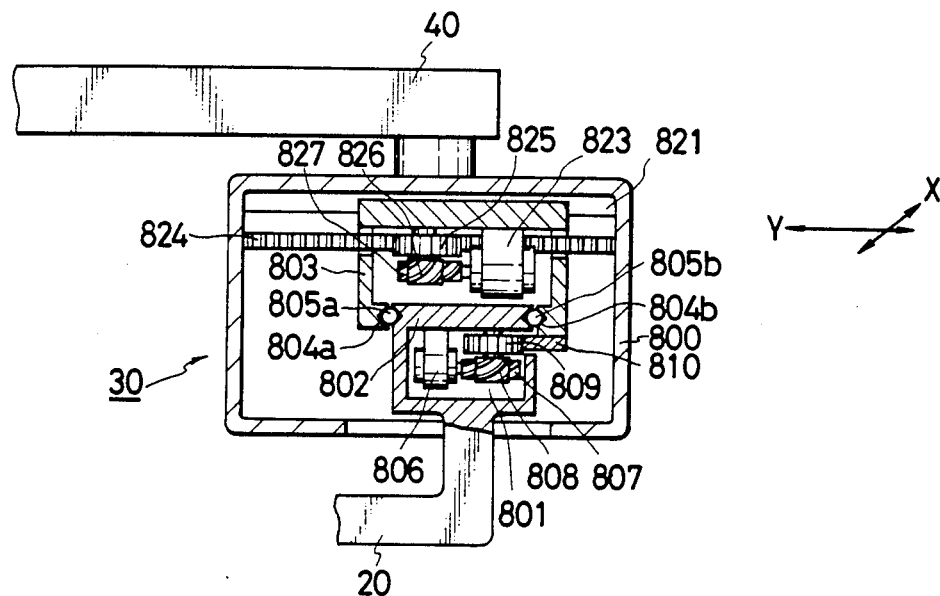
FIG. 10 is a fragmentary sectional view showing details of the fine adjustment device; and, FIG. 11 is a sectional view showing details of the bed moving mechanism.

Referring to FIG. 10, it will be noted that the fine adjustment device 30 includes a rail section 802 which is intergral with the upper end of the support arm 20 and formed at the opposite sides with V-shaped grooves 802a and 802b. A transversely movable member 803 is carried by the rail section 802 and has V-shaped grooves 804a and 804b which are opposed to the grooves 802a and 802b on the rail section 802. Bearing balls 805a and 805b are disposed between each pair of V-shaped grooves 802a, 804a and 802b, 804b so that the member 803 is slidable in X-direction. Beneath the rail section 802, there is formed a space 801 wherein a pulse motor 806 is located and supported by the rail section 802. The pulse motor 806 has an output shaft formed with a worm 807 which is meshed with a pinion 808 which is integral with a pinion 809 rotatably supported on the rail section 802. The pinion 809 is in meshing engagement with a rack 810 provided on the transversely movable member 803. Thus, the support arm 20 can be moved in the X-direction by the pulse motor 806 under the signal from the operation circuit 207.

The transversely movable member 803 has a rail follower 820 which is guided by Y-direction rails 821 and in turn carries a pulse motor 823 which has an output shaft formed with a worm 827. The worm 827 is in meshing engagement with a pinion 826 which is integral with a pinion 825 engaged with a rack 824. The rack 824 extends in Y-direction and provided on a casing 800 of the fine adjustment mechanism 30 which is carried by the arm 40. Thus, the member 803 and therefore the support arm 20 can be moved in the Y-direction under the signals from the operation circuit 207.

Figure 6:
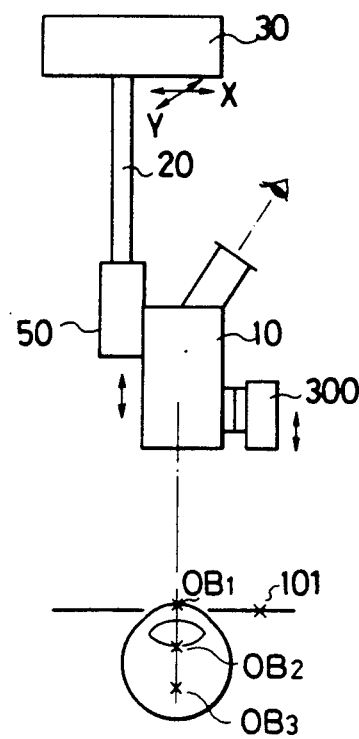
FIG. 6 is a side view of the microscope in accordance with another embodiment of the present invention.

Referring now to FIG. 6, there is shown another embodiment of the present invention which has a detection system 300 separated from the observing optical system. In this instance, the patient's eye has three portions $OB_1$, $OB_2$ and $OB_3$ of different distances from the observing optical system 10 of the operation microscope 10. The operator adjusts the microscope through the focusing mechanism 50 and the fine adjustment device 30 so that the observing optical system 10 is focused at one of the portions $OB_1$, $OB_2$ and $OB_3$. As in the previous embodiment, the detecting system 300 produces signals concerning the visual field and the focusing condition of the observing optical system 10 and the signals are memorized. The detecting system 300 is kept always in operation so that, whenever the visual field and/or the focusing condition of the microscope and changed, correcting signals are produced and the focusing mechanism 50 and the fine adjustment device 30 are actuated to correct the changes.

Figure 7:
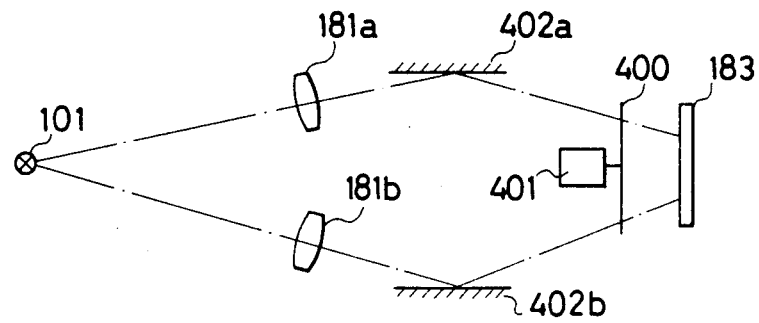
FIG. 7 is a diagrammatical illustration of a mark detecting system in accordance with a further embodiment of the present invention.

In FIG. 7, there is shown another example of detecting system which uses only a single light emitting diode 101 for detecting the visual field and the focusing condition of the microscope. In this arrangement, the light beams emitted from the diode 101 are passed on one hand through a first optical path comprised of an imaging lens 181a and a mirror 402a and on the other hand through a second optical path comprised of an imaging lens 181b and a mirror 402b. The light beams through these paiths are passed alternately to a detector 183 by means of a rotating chopper 400 which is adapted to be rotated by a motor 401.

Figure 8A:
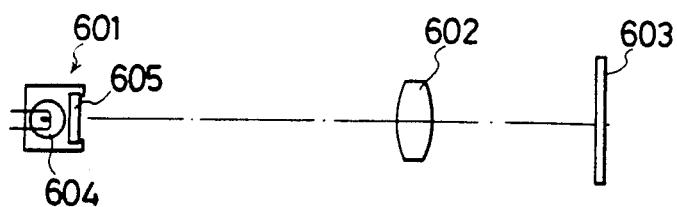
FIG. 8 (A), (B), (C) show a further example of the mark detecting system.
Figure 8B:
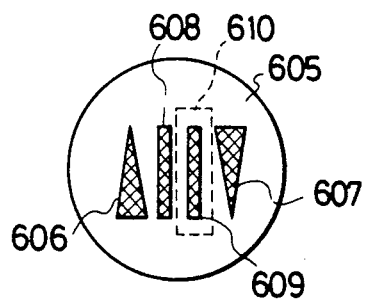

FIG. 8 shows a further embodiment of detecting system. As shown in FIG. 8(A), the system includes a pattern projecting device 601 including a light source 604 and a pattern plate 605 having a pattern as shown in FIG. 8(B). The light beams projected from the device 601 are passed through a projecting lens 602 to be focused at a detector 603 constituted by a linear array of photoelectric elements. The pattern on the plate 605 includes a pair of substantially triangular or wedge-shaped marks 606 and 607 and a pair of parallel linear marks 608 and 609. One of the linear mark 609 has a glass plate 610 attached thereto so that the mark 609 is focused at a distance different from the point where the mark 608 is focused.

Figure 8C:
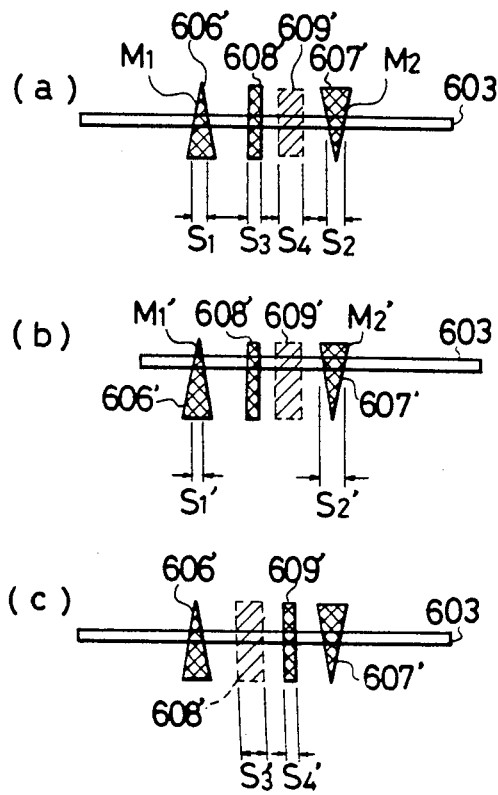

FIG. 8(C) shows in (a) a projection of the marks on the detector 603 at the initial position of the microscope. On the detector 603, the projection 606' of the mark 606 has a width $S_1$. Similarly, the projections 607', 608' and 609' of the marks 607, 608 and 609 have widths $S_2$, $S_3$ and $S_4$, respectively. Further, the centers of the projections 606' and 607' are detected as being at the positions $M_1$ and $M_2$, respectively. When there is any change in the visual field, the widths of the projections 606' and 607' change to values $S_1'$ and $S_2'$, respectively, as shown in FIG. 8C(b). Further, the positions of the centers of the projections 606' and 607' are changed to $M_1'$ and $M_2'$, respectively. It is therefore possible to detect the direction and the amount of displacement. Further, when there is any change in the focal condition, there will be changes in the widths of the projections 608' and 609' as shown by $S_3'$ and $S_4'$ in FIG. 8C(c).

Figure 9:
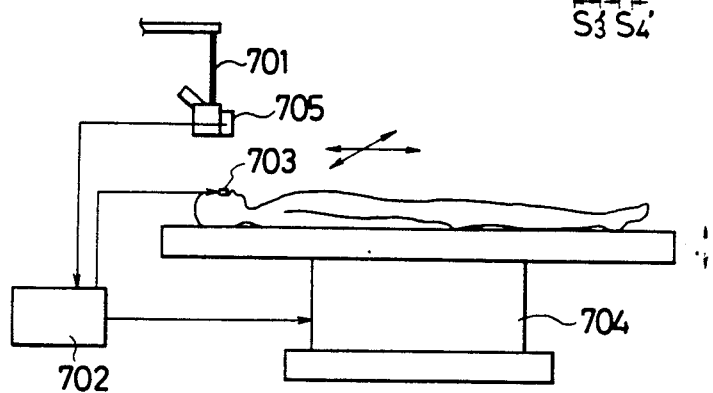
FIG. 9 is a side view showing a further embodiment of the present invention.
Figure 11:
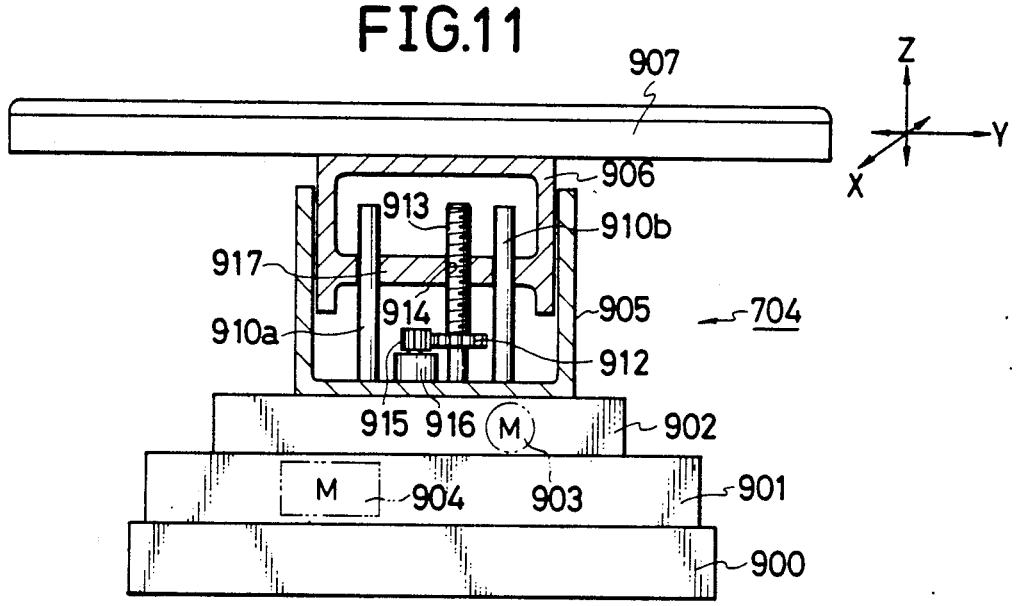

In the embodiment shown in FIG. 9, the operation microscope 701 has a detecting device 705 constituted in accordance with one of the previously described embodiments. Beneath the microscope 701, there is a bed 704 for supporting a patient and a mark projecting device in accordance with anyone of the previous embodiments is attached to the patient. The bed 704 is movable in a horizontal plane and in a vertical direction. The output of the detecting device 705 is connected with a control circuit 702 which has arrangements as shown in FIG. 3. FIG. 11 shows a bed driving mechanism which includes a stationary base 900 carrying a transversly movable carriage 901 for a movement in Y-direction. The carriage 901 carries a longitudinally movable carriage 902 for movement in X-direction. A motor 904 is provided for moving the carriage 901 in the Y-direction through for example a mechanism as shown in FIG. 10. A second motor 903 is similarly provided for moving the carriage 902 in the X-direction. The carriage 902 carries a housing 905 in which a post 906 for supporting a bed frame 907 is vertically slidably received. In the housing 905, there are provided guide posts 910a and 901b which are slidably engaged with holes in the bottom wall 917 of the post 906 to guide the post 906 in the vertical direction. The bottom wall 917 of the post 906 is formed with a threaded hole 914 which is engaged with a vertical screw shaft 913 rotatably provided on the housing 905. The screw shaft 913 has a pinion 912 which is in engagement with a pinion 915 provided on an output shaft of a motor 916 on the housing 905. The output signals of the control circuit 702 operate the motors 903, 904 and 916 to move the bed 704 in a horizontal and/or vertical direction so that any change in the visual field and/or focus condition of the microscope 701 can be corrected.

The invention has thus been shown and described with reference to specific embodiments, however, it should be noted that the invention is in no way limited to the details of the illustrated arrangements but changes and modifications can be made without departing from the scope of the appended claims.

We claim:

1. An operation microscope system comprising operation microscope means including observation optical means having an observing optical axis and adapted for observing at least a portion of a patient wherein an operation is to be made, support means for supporting said microscope means and at least said portion of the patient for relative movement, driving means for effecting a relative movement between said portion of the patient and said microscope means, mark means provided on one of said microscope means and said patient, mark detecting means provided on the other of the microscope means and said patient for receiving beams from said mark means to produce a position signal in accordance with a relative position between the mark means and the mark detecting means, memory means for memorizing an initial position signal as produced by said detecting means when an initial relative position is established between said portion of the patient and said microscope means, displacement detecting means for detecting a relative displacement between said portion of the patient and the microscope means based on said initial position signal and an actual position signal as produced by said mark detecting means to produce a displacement signal, adjusting means for actuating said driving means in accordance with said displacement signal to restore said initial relative position.

2. An operation microscope in accordance with claim 1 in which said support means includes means for supporting said microscope means and said portion of the patient so that a relative movement is allowed between said portion of the patient and the microscope means at least in a plane perpendicular to the observing optical axis for a visual field adjustment, said driving means including means for effecting the relative movement in said plane.

3. An operation microscope in accordance with claim 2 in which said support means includes a patient support for supporting at least said portion of the patient for movement with respect to the microscope means.

4. An operation microscope in accordance with claim 2 in which said support means includes means for supporting the microscope means for movement with respect to said portion of the patient.

5. An operation microscope in accordance with claim 1 in which said support means includes means for supporting said microscope means and said portion of the patient so that a relative movement is allowed between said portion of the patient and the microscope means in a direction parallel to said optical axis for focusing, said driving means including means for effecting the relative movement along said optical axis.

6. An operation microscope in accordance with claim 5 in which said support means includes a patient support for supporting at least said portion of the patient for movement in the direction parallel to the optical axis.

7. An operation microscope in accordance with claim 5 in which said support means includes focusing means provided in said microscope means and the driving means includes means for driving the focusing means.

8. An operation microscope in accordance with claim 1 in which said mark means includes at least two light-emitting elements, said mark detecting means including two-dimensional arrays of photoelectric elements so that the mark detecting means produces signals representing positions in terms of coordinates values on the two-dimensional arrays.

9. An operation microscope system comprising operation microscope means including observation optical means having an observing optical axis and adapted for observing at least a portion of a patient wherein an operation is to be made, mark means provided on one of the microscope means and said patient in the vicinity of said portion, means for focusing said observation optical means at said portion of the patient, mark detecting means provided on the other of the microscope means and said patient for receiving beams from said mark means to produce a position signal in accordance with a relative position between the mark means and the mark detecting means, memory means for memorizing an initial position signal as produced by said detecting means when an initial focus condition is established between said portion of the patient and said microscope means, out-of-focus detecting means for detecting a relative displacement between said portion of the patient and the microscope means based on said initial position signal and an actual position signal as produced by said mark detecting means to produce an out-of-focus signal, adjusting means for actuating said focusing means in accordance with said out-of-focus signal to restore said initial focus condition.

10. An operation microscope system comprising operation microscope means including observation optical means having an observing optical axis and adapted for observing at least a portion of a patient wherein an operation is to be made, mark means provided on one of the microscope means and said patient in the vicinity of said portion, means for moving said observation optical means with respect to said portion of the patient in a plane perpendicular to said observation optical axis, mark detecting means provided on the other of the microscope means and said patient for receiving beams from said mark means to produce a position signal in accordance with a relative position between the mark means and the mark detecting means, memory means for memorizing an initial position signal as produced by said detecting means when an initial relative position is established between said portion of the patient and said microscope means, displacement detecting means for detecting a relative displacement between said portion of the patient and the microscope means in a plane perpendicular to the observing optical axis based on said initial position signal and an actual position signal as produced by said mark detecting means to produce a displacement signal, adjusting means for actuating said moving means in accordance with said displacement signal to restore said initial relative position.

* * * * *